United States Patent [19]

Kohli

[11] Patent Number: 4,992,575
[45] Date of Patent: Feb. 12, 1991

[54] PROCESS FOR THE PREPARATION OF N,N'-DIMETHYL AROMATIC DIAMINES, INTERMEDIATES AND PRODUCTS

[75] Inventor: Dalip K. Kohli, Norwalk, Conn.

[73] Assignee: American Cyanamid Company, Stamford, Conn.

[21] Appl. No.: 252,224

[22] Filed: Sep. 30, 1988

Related U.S. Application Data

[62] Division of Ser. No. 826,168, Feb. 5, 1986, Pat. No. 4,778,900.

[51] Int. Cl.$^5$ .................. C07C 229/00; C07C 211/00
[52] U.S. Cl. ........................................ 560/49; 560/19; 560/50; 564/305; 564/307; 564/331; 564/413; 564/430; 564/440
[58] Field of Search ............... 564/305, 307, 331, 413, 564/430, 440; 528/64; 560/50, 19, 49

[56] References Cited

U.S. PATENT DOCUMENTS

| | | | |
|---|---|---|---|
| Re. 32,677 | 5/1988 | Rasshofer | 528/64 |
| 3,846,351 | 11/1974 | Huffaker | 528/64 |
| 4,532,317 | 7/1985 | Rasshofer | 528/64 |
| 4,578,446 | 3/1986 | House | 528/64 |

Primary Examiner—Robert A. Wax
Assistant Examiner—F. Tsung
Attorney, Agent, or Firm—Roger S. Benjamin

[57] ABSTRACT

N,N'-dimethyl aromatic diamines are prepared from the corresponding diprimary amines via a two step synthesis forming first the corresponding di-succinylimidomethylamine and then reductively cleaving the succinylimido group. The products are useful, e.g., as epoxy curing agents.

3 Claims, No Drawings

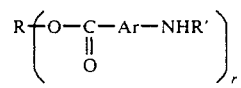

PROCESS FOR THE PREPARATION OF N,N'-DIMETHYL AROMATIC DIAMINES, INTERMEDIATES AND PRODUCTS

This is a divisional of co-pending patent application Ser. No. 06/826,168, filed on Feb. 5, 1986 now U.S. Pat. No. 4,778,900.

FIELD OF THE INVENTION

This invention relates to a method and intermediates useful in the preparation of N,N'-dimethyl aromatic diamines, to such compounds, and to their use as epoxy curatives, and in other applications.

CROSS REFERENCE TO RELATED APPLICATIONS

This application is related to the following concurrently filed applications:

| Ser. No. | Applicant(s) |
|---|---|
| 06/518,872 Now Abandoned | D. W. Wang J. L. Courter D. K. Kohli |
| 06/518,872 Now U.S. Pat. No. 4562217 | K. Hirschbuehler |
| 06/518,874 Now U.S. Pat. No. 4623681 | K. Hirschbuehler D. K. Kohli |
| 06/518,879 Now U.S. Pat. No. 4558,078 | D. R.Draney D. K. Kohli |

BACKGROUND OF THE INVENTION

Description of the Prior Art

Polyamines react with epoxide prepolymers to cure them by a polyaddition reaction to form tough, resinous compositions having utility as encapsulants for electronic components, adhesives, coatings, and the like. When filled, and reinforced, e.g., with glass or graphite fibers such compositions, especially those made from aromatic polyamines and epoxy prepolymers provide structural composites useful where high strength and toughness are required, for example in aircraft.

Aromatic polyamines corresponding to the following general structure are generally known to be useful in such polyaddition reactions:

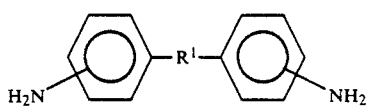

wherein $R^1$ is

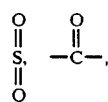

any alkyl or aryl divalent radical, and such radicals terminated, interrupted or interrupted and terminated by —O—, —S— and

Moreover, aromatic polyamines corresponding to the general formula:

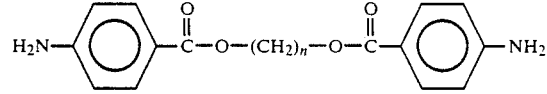

in which R is derived from, e.g., an aliphatic diol, Ar represents, e.g., phenylene and R' represents, e.g., hydrogen or an alkyl radical, and r is, for example, 2, are described in U.K. Patent No. 1,182,377 to be useful to form polyaddition products with epoxide compounds having more than one epoxide group per molecule. Such products are disclosed to be useful as bonding agents in the production of moldings, coatings, laminates, especially glass-filled laminates, and molding compositions. From page 3, line 117, to page 4, line 3, a distinct preference is stated for compounds wherein R' is hydrogen.

In U.S. Pat. No. 3,932,360, diamine cured polyurethane products are described, in which the diamines are of the formula, e.g., $$H_2N-\underset{}{\bigcirc}-\overset{O}{\underset{\|}{C}}-O-(CH_2)_n-O-\overset{O}{\underset{\|}{C}}-\underset{}{\bigcirc}-NH_2$$

wherein n is an integer from 2 to 12. This patent does not describe any N-alkyl substituted diamines.

N-methyl derivatives of such amines have now been found to comprise an important family of epoxy resin curing agents. It is, therefore, desirable to provide a general method to prepare N-alkyl substituted diamines in light of their ability to provide, for example, epoxide polyaddition compositions with improved properties.

SUMMARY OF THE INVENTION

It is an object of the present invention to provide a novel general process to produce N,N'-dimethyl diamine compounds.

It is a further object of this invention to provide novel N,N'-dimethyl diamine compounds, which are useful, for example, as curing agents suitable for use with compounds having more than one epoxide group per molecule.

It is still another object of this invention to provide novel N-succinylimidomethyl diamino compounds useful as intermediates to produce such N,N'-dimethyl aromatic diamines.

To this end, there is provided a method for the preparation of a bis-N-methylamino aromatic compound comprising (a) reacting the corresponding diprimary amino aromatic compound with succinimide and formaldehyde until formation of the corresponding bis-N-succinimidyl methylamino aromatic compound is substantially complete; and (b) treating the product of step (a) with sodium borohydride in a solvent until formation of the bis-n-methylamino aromatic compound is substantially complete.

In another aspect, the invention provides compounds of the formula:

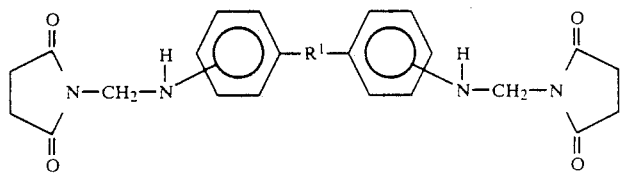

wherein R¹ is as above defined. These novel intermediates are useful, for example, to produce N,N'-dimethyl aromatic diamines.

In another feature, the present invention provides compounds of the formula:

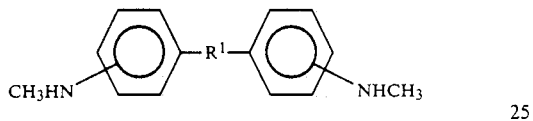

wherein the CH₃NH groups are in the 4 and 4' positions and R¹ is

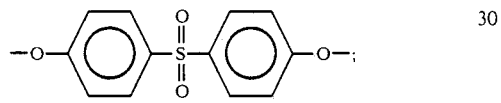

the CH₃NH— groups are in the 3 and 3' positions and R¹ is

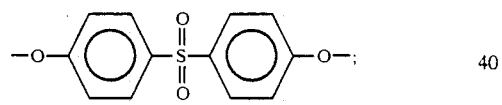

the CH₃NH— groups are in the 4 and 4' positions and R¹ is

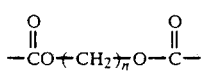

and n is an integer of from 2 to 12; the CH₃NH— groups are in the 2 and 2' positions and R¹ is —SCH₂CH₂S— ; and the CH₃NH— groups are in the 3 and 3' positions and R¹ is

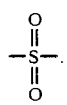

These compounds provide, for example, polyaddition reaction products with polyepoxides having high strength and toughness.

DETAILED DESCRIPTION OF THE INVENTION

The process is broadly applicable to primary aromatic polyamines. These are illustrated above by formula, but preferably group R¹ will be

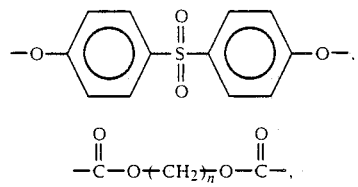

wherein n is 2 to 12,

, or

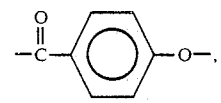

Also illustrative examples are amines in which R¹ is

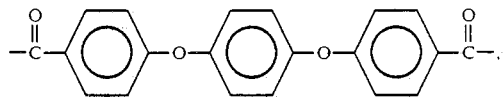

and the like.

Such compounds are either commercially available or they can be readily prepared by those skilled in this art.

The di-primary amines used as certain of the starting materials are also described in the above-mentioned U.S. Pat. No. 3,932,360. In general, they are prepared by reacting p-nitrobenzoyl chloride with a diol and reducing the thus formed compound to a diamine. Illustrative of suitable diols are ethylene glycol, 1,3-propanediol, 1,4-butanediol, 1,5-pentanediol, and 1,6-hexanediol. Preferred is 1,3-propanediol. The preferred diamine starting material is 1,3-propanediol-bis-p-amino benzoate.

As a general procedure, succinimide is reacted with the diamine to produce the corresponding and novel di-succinimidomethyl-substituted diamine. At least a stoichiometric amount of the succinimide will be used. A solvent, such as ethanol, and heating, e.g., at temperatures of from 40° C. to 120° C. facilitate the reaction. In refluxing ethanol, formation of the disuccinimidomethyl substituted compound is substantially complete in from 2 to 12 hours. The product, which can be recovered by conventional methods, is generally obtained in excellent yield. Typically, yields of greater than 80% of theoretical are obtained. In the next step of the process, the bis-succinimidomethyl compound is treated under conditions which lead to formation of the bis-N-methyl-amino compound. This is conveniently accomplished by using a combination of a borohydride and a solvent, e.g., an aprotic solvent. Typically, a mixture of sodium borohydride and dimethyl sulfoxide is used. The product is recovered in conventional ways. It is obtained in high yield.

Use of the new compounds as curing agents for epoxy resin is shown hereinafter.

DESCRIPTION OF THE PREFERRED EMBODIMENTS

The following non-limiting examples illustrate the preparation of representative novel compounds of the present invention and shows their use as curing agents.

EXAMPLE 1

(a)

N,N'-Disuccinimidomethyl-1,3-trimethylene-bis(p-aminobenzoate).

Two moles of succinimide are reacted with one mole of 1,3-propanediol bis-p-aminobenzoate in refluxing ethanol for 6 hours; and the product is recovered by filtration after cooling, m.p. 198–200° C., yield 82% of theoretical.

(b)

N,N'-Dimethyl-1,3-trimethylene-bis-(p-aminobenzoate).

The intermediate of step (a) is treated in dimethyl sulfoxide with sodium borohydride at 85° C. for 1 hour. The mixture is poured into water, the product precipitates and is recovered by filtration, m.p. 114° C. after recrystallization from methylene chloride-cyclohexane mixture, yield 84% of theoretical.

EXAMPLE 2

By the general procedure of Example 1, step (a), substituting the corresponding diprimary amines, the following di-N-succinimidomethyl amines can be provided:

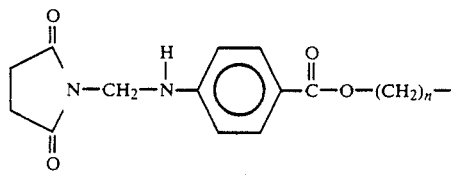

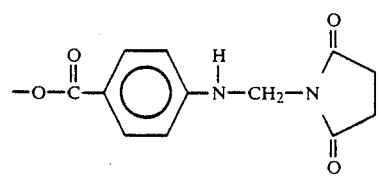

wherein n is, respectively, 2, 4, 5 and 6.

By the general procedure of Example 1, step (b), substituting the corresponding N-succinimidomethyl amines, the following N-methyl amines can be obtained:

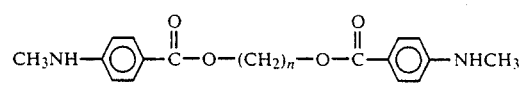

wherein n is, respectively, 2, 4, 5, and 6.

EXAMPLE 3

(a)

N,N'-Disuccinimidomethyl-4,4'-bis(p-aminophenoxy) diphenyl sulfone.

The general procedure of Example 1, step (a) is repeated substituting for the bis-aminobenzoate compound, 4,4'-bis(p-aminophenoxy)diphenyl sulfone.

(b) N,N'-Dimethyl-4,4'-bis(p-amino)diphenyl sulfone.

The procedure of Example 1, step (b), was repeated, substituting the intermediate of step (a) herein. The named product, m.p. 73–75° C., was obtained.

EXAMPLE 4

(a)

N,N'-Disuccinimidomethyl-4,4'-bis(m-aminophenoxy) diphenyl sulfone.

The procedure of Example 1, step (a) is repeated, substituting 4,4'-bis(m-amino-phenoxy) diphenyl sulfone.

(b) N,N'-Dimethyl-4,4'-bis(m-aminophenoxy)diphenyl sulfone.

The procedure of Example 1, step (b), was repeated, substituting the intermediate of step (a) herein. The named product, m.p., 63–65° C., was obtained.

The products of the examples are mixed with epoxide prepolymers at 135° C. for 10 minutes and then degassed under vacuum. The compositions are cured by casting in a mold and cured for two hours at 135° C. and then for 3 hours at 180° C. Physical properties are measured by ASTM D-790, Method 1 and dynamic-mechanical analysis according to ASTM D-4065. The formulations used and the results obtained are set forth in the Table:

TABLE

| Composition | Epoxy/N-methyldiamine Compositions | | | |
| --- | --- | --- | --- | --- |
| | A | B | C | D |
| Formulation (parts by weight) | | | | |
| N,N,N',N'-Tetra-glycidyl-4,4-diamino-diphenyl methane | 100 | 100 | 100 | 100 |
| N,N'-Dimethyl-1,3-trimethylene bis(p-aminobenzoate)(Ex. 1) | 109 | — | — | — |
| N,N'-Dimethyl-4,4'-bis(p-aminophenoxy)diphenyl sulfone (Ex. 2) | — | 92 | 92 | — |
| N,N'-Dimethyl-4,4'-bis(m-aminophenoxy)diphenyl sulfone (Ex. 3) | — | — | — | 147 |
| 4,4'-bis(m-aminophenoxy)diphenyl | — | 21.6 | 30 | — |

TABLE-continued

| Composition | Epoxy/N-methyldiamine Compositions | | | |
| --- | --- | --- | --- | --- |
| | A | B | C | D |
| sulfone | | | | |
| Properties | | | | |
| Modulus, MSI dry | 0.48 | 0.56 | 0.58 | 0.60 |
| wet | 0.22 | 0.39 | 0.40 | 0.44 |
| Strength, KSI dry | 22 | 20.4 | 19.0 | 20.0 |
| Strain, % dry | >10 | 4.0 | 3.6 | 3.5 |
| Work to break, in-lbs/in$^3$ | >1600 | 455 | 385 | 385 |
| Tg, °C. dry/wet | 165/137 | 186/162 | 191/159 | 162/134 |

In light of the above description, it is obvious that advantageous results have been obtained with the present invention. The state-of-the-art synthetic methods are limited in scope and utilize a number of steps, whereas the method of this invention is generally applicable and provides high yields in only two steps. By using the bis-methylamino compound of this invention as an epoxy curative, resins can be obtained with improved strength, toughness and hot/wet properties. The new resins can be used for fiber reinforced composites where high strength and toughness are required, for example, in aerospace primary or secondary structures and other similar applications, e.g., automobiles. They can also be used in adhesives.

The above-mentioned patents are incorporated herein by reference. Many variations will suggest themselves to those skilled in this art in light of the above disclosure. All such obvious variations are within the full intended scope of the appended claims.

What is claimed is:

1. A method for the preparation of a bis-N-methylamino aromatic compound comprising:

(a) reacting a diprimary amino aromatic compound of the formula:

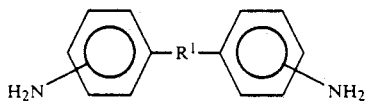

wherein R$^1$ is selected from a direct bond, divalent alkylene of 1 to 20 carbon atoms,

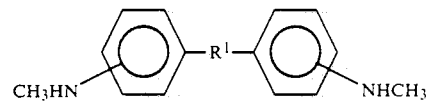

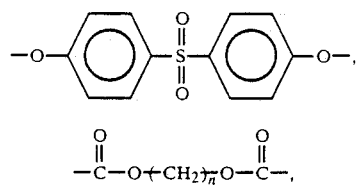

wherein n is 2 to 12,

—S—CH$_2$CH$_2$—S, with succinimide and formaldehyde to form the corresponding bis-N-succinimidyl methylamino aromatic compound; and (b) treating the product of step (a) with sodium borohydride in a solvent to form a bis-N-methylamino aromatic compound as product, said compound having the formula:

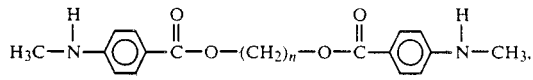

wherein R$^1$ is above-identified.

2. A method for the preparation of a bis-N-methyl amino compound of the formula:

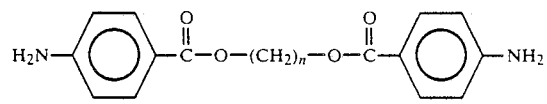

wherein n is an integer of from 2 to 6 comprising (a) reacting the corresponding diprimary amino compound of the formula:

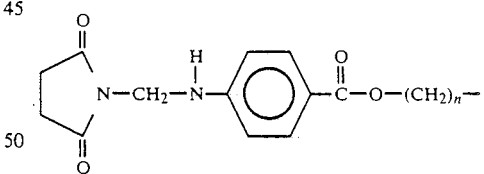

wherein n is as above defined, with succinimide and formaldehyde, until formation of a compound having the formula:

wherein n is as above defined; and (b) treating said reaction product with sodium borohydride and dimethylsulphoxide until formation of said bis-N-methyl amino compound is substantially complete.

3. A method as defined in claim 2 wherein, in each of said compounds, n is 3.

* * * * *